(12) United States Patent
Vives Florez et al.

(10) Patent No.: US 10,576,114 B2
(45) Date of Patent: Mar. 3, 2020

(54) **COMPOSITION COMPRISING BACTERIOPHAGES FOR REDUCING, ELIMINATING AND/OR PREVENTING *SALMONELLA ENTERITIDIS*, *SALMONELLA TYPHIMURIUM* AND *SALMONELLA PARATYPHI* B**

(71) Applicant: UNIVERSIDAD DE LOS ANDES, Bogota (CO)

(72) Inventors: Martha Josefina Vives Florez, Bogota (CO); Ana Paula Jimenez Sanchez, Bogota (CO); Angela Victoria Holguin Moreno, Bogota (CO)

(73) Assignee: UNIVERSIDAD DE LOS ANDES, Bogota (CO)

( * ) Notice: Subject to any disclaimer, the term of this patent is extended or adjusted under 35 U.S.C. 154(b) by 62 days.

(21) Appl. No.: 15/779,371

(22) PCT Filed: Nov. 21, 2016

(86) PCT No.: PCT/IB2016/057014
§ 371 (c)(1),
(2) Date: Aug. 31, 2018

(87) PCT Pub. No.: WO2017/089947
PCT Pub. Date: Jun. 1, 2017

(65) Prior Publication Data
US 2019/0070231 A1 Mar. 7, 2019

(30) Foreign Application Priority Data
Nov. 25, 2015 (CO) .................... 15281747

(51) Int. Cl.
| | |
|---|---|
| A61K 35/76 | (2015.01) |
| C12N 7/00 | (2006.01) |
| A23K 10/18 | (2016.01) |
| A23K 50/75 | (2016.01) |
| A61L 2/00 | (2006.01) |
| A23K 20/153 | (2016.01) |
| A61P 31/04 | (2006.01) |
| A61K 9/12 | (2006.01) |
| A61K 9/70 | (2006.01) |
| A61K 38/16 | (2006.01) |

(52) U.S. Cl.
CPC ............. *A61K 35/76* (2013.01); *A23K 10/18* (2016.05); *A23K 20/153* (2016.05); *A23K 50/75* (2016.05); *A61K 9/12* (2013.01); *A61K 9/7015* (2013.01); *A61K 38/162* (2013.01); *A61L 2/00* (2013.01); *A61P 31/04* (2018.01); *C12N 7/00* (2013.01); *A01K 2227/30* (2013.01); *A23V 2002/00* (2013.01); *C12N 2795/10021* (2013.01); *C12N 2795/10031* (2013.01); *C12N 2795/10032* (2013.01); *C12N 2795/10121* (2013.01); *C12N 2795/10131* (2013.01); *C12N 2795/10132* (2013.01)

(58) Field of Classification Search
None
See application file for complete search history.

(56) References Cited

U.S. PATENT DOCUMENTS

| | | |
|---|---|---|
| 6,322,783 B1 | 11/2001 | Takahashi |
| 2003/0113293 A1 | 6/2003 | Bermudes et al. |
| 2006/0094076 A1 | 5/2006 | Stave et al. |
| 2008/0118468 A1 | 5/2008 | Sulakvelidze et al. |
| 2009/0304638 A1 | 12/2009 | Yoon et al. |
| 2010/0135962 A1 | 6/2010 | Kang et al. |
| 2010/0158870 A1 | 6/2010 | Kang et al. |
| 2011/0052544 A1 | 3/2011 | Shin et al. |
| 2012/0294892 A1 | 11/2012 | Choi et al. |
| 2014/0219968 A1 | 8/2014 | Llagostera et al. |
| 2014/0220659 A1 | 8/2014 | Dastych et al. |

OTHER PUBLICATIONS

Search Report dated Dec. 4, 2017 for Colombian Application No. 15281747.

*Primary Examiner* — Michelle S Horning
(74) *Attorney, Agent, or Firm* — Lucas & Mercanti, LLP

(57) ABSTRACT

The present invention relates to a new cocktail of bacteriophages with specific lytic activity against *Salmonella enteritidis*, *Salmonella typhimurium* and *Salmonella paratyphi* B., for reducing, eliminating and/or preventing them in farm animals and animals from the poultry sector, such as poultry, hens and breeding hens, in addition to eggs. It may be administered as an additive in the feed, in water or by spray. Moreover, the cocktail may be used as a disinfectant in work areas of farms and abattoirs, and in processed foods, without affecting the organoleptic properties of the product.

20 Claims, 2 Drawing Sheets
Specification includes a Sequence Listing.

Figures

COMPOSITION COMPRISING BACTERIOPHAGES FOR REDUCING, ELIMINATING AND/OR PREVENTING *SALMONELLA ENTERITIDIS, SALMONELLA TYPHIMURIUM* AND *SALMONELLA PARATYPHI* B

FIELD OF THE INVENTION

The present invention relates to a new cocktail of bacteriophages with specific lytic activity against *Salmonella enteritidis*, *Salmonella typhimurium* and *Salmonella paratyphi* B., for reducing, eliminating and/or preventing them in farm animals and animals from the poultry sector, such as poultry, hens and breeding hens.

BACKGROUND OF THE INVENTION

*Salmonellosis* is one of the main causes of bacterial gastroenteritis in humans (Brenner, et al. 2000). Each year, 93.8 million cases are reported globally, giving high indices of morbidity and mortality (155 000 deaths/year) (Majowicz, et al. 2010; Cabrera, 2008). In the United States it is estimated that 40% of the infections caused by *Salmonella* occur in children under 10 years (Angulo, et al. 2004). Treatment of this disease imposes a considerable economic burden on many countries; according to the United States Department of Agriculture (USDA), the annual cost for treating *salmonellosis*, including loss of productivity, in 2005 was 2.3 billion dollars (Atterbury, 2007). Usually these pathogens cause mild and moderate gastroenteritis, but in more severe cases they may cause septicemias (Zhao, et al. 2001).

Transmission of *Salmonella* is mainly due to consumption of contaminated foods, in particular by consuming poultry products, which are widely accepted as the main source of infection with this bacterium (Atterbury, 2007).

The USDA estimates that 50-75% of the cases of *salmonellosis* are due to the purchase of contaminated poultry products, in particular through consumption of chicken and eggs. The most prevalent serovars worldwide include *Salmonella enteritidis* (64.5%) and *Salmonella typhimurium* (16.5%) (WO2004071324 A2; EP 2 550 870 A1). However, in 2010 the group for Integrated Investigation and Vigilance of Antimicrobial Resistance—COIPARS of the Colombian Corporation for Agricultural Research—CORPOICA, after reporting a prevalence of *Salmonella* of 41% in chicken-producing farms and 26% in chicken at points of sale, found that the serovars of *Salmonella paratyphi* B and *Salmonella Heidelberg* were the most prevalent in farms in Colombia (Donado-Godoy, et al. 2012). Regarding *Salmonella paratyphi* B, there was a prevalence in farms of 76% and in meat at points of sale of 51%, whereas *Salmonella Heidelberg* had a prevalence of 23% and 16%, respectively (Donado-Godoy, 2010). This report was of great importance in the sector since it was the first time that *Salmonella paratyphi* B had been reported in the food chain of the poultry sector. Based on this publication, a study was conducted in which isolates of *Salmonella* were serotyped at various points of the poultry chain, including workers in the sector. As a result, the serotypes isolated from farms and abattoirs were exactly the same as found in humans, company workers (personal communication). The earlier study shows that the increase in serotypes isolated as *Salmonella paratyphi* B are reaching humans and therefore may be generating new outbreaks of a pathogenic *Salmonella* that was not being controlled and that may become a new public health problem.

One of the reasons why there is a high prevalence of *Salmonella* in foods of poultry origin is due to their capacity for colonizing the intestine of chicken; in the case of *Salmonella enteritidis*, *Salmonella typhimurium* and *Salmonella paratyphi* B, they do not produce infection or visible symptoms in the bird and they have the capacity to colonize the interior of eggs. However, they cause disease in humans who consume contaminated poultry products because *Salmonella* crosses the intestinal barrier, destroying the microvilli of the epithelial cells and in consequence affecting the capacity for absorption (Zhao, 2002; Keller, et al. 1995).

Control of *Salmonella* in the poultry chain has been based historically on a combination of biosafety in the farm, taking appropriate sanitary measures for housing, production and marketing, in addition to the use of antimicrobials and vaccines (Atterbury, 2007). Contamination in poultry farms is the result of infected birds and cross contamination in the production chain (San Myint, 2004; Carrasco, et al. 2012). Cross contamination occurs owing to failure to implement good manufacturing practice, where lack of hygiene, and mistakes in the steps of refrigeration and transport of the products, mean that the conditions of biosafety in the production chain are not the most appropriate (Carrasco, et al. 2012; San Myint, 2004). In any case, the initial source of contamination by *Salmonella* is due to the state of the infected poultry. The importance of the foregoing lies in control of the bacterium from its initial inoculum, so as to reduce contamination by *Salmonella* in the subsequent steps of the production process for poultry-based food products (San Myint, 2004).

The cost of the treatments that are used for reducing *Salmonella* in chicken farms and in foods is high because they are widely distributed pathogens and they colonize easily (Zhao, 2002; WO 2004071324 A2). That is why various treatments have been implemented for controlling and reducing these pathogens such as the use of chlorinated water in sprays, physical treatments such as steam cleaning, dry heat and ultraviolet light, and the use of chemical additives. However, in some cases it has been reported that the organoleptic quality of the final product may be affected (Garcia, et al. 2008). Regarding the use of disinfectants, these have been used for eradicating the pathogens and for reducing cross contamination during the production process, but the appearance of resistance and the environmental consequences mean that it is not fully effective (Goode, et al. 2003). Another treatment widely used throughout the world for controlling *Salmonella* serovars in the poultry industry is vaccination. There are reports that show cases of low efficiency, since the vaccines that are used most are made from inactivated or attenuated reference strains that do not cover all of the serotypes present in all poultry farms (Zhao, 2002; Vandelplas, et al. 2010). Moreover, the vaccines are only directed at controlling *Salmonella enteritidis* and *Salmonella typhimurium*, but not *Salmonella paratyphi* B, a new emerging pathogen in the Colombian poultry sector, and that has previously occurred in several European countries, which makes its control even more difficult (Donado-Godoy, et al. 2012; Van Immersel, et al. 2004).

Antimicrobials have been used in agriculture since the beginning of 1950 for treating bacterial infections and to improve feed efficiency both in the cattle-raising sector and in the poultry sector (Angulo, et al. 2004). In recent years, the overuse of antimicrobials in the poultry industry has resulted in the appearance of *Salmonella* strains that are resistant to these medicinal products (INS, 2011). The problem is that most of them are used for controlling bacteria in animals for human consumption and in hospitalized patients who require clinical treatment. As a result, this increases the probability of zoonotic bacteria developing resistance to the medicinal products used in humans (Angulo, et al. 2004). The emergence of multi-drug resistant (MDR) *Salmonella* strains is of great concern to the medical and veterinary professions, since according to epidemiological studies, the commonest source of MDR strains in humans is due to the consumption of contaminated foods of animal origin (O'Flynn et al., 2006).

Faced with the need for new strategies for controlling, eliminating and/or reducing *Salmonella* in the poultry industry, phage-therapy has become very important in recent years since the results are promising. Bacteriophages are viruses that kill bacteria and they are widely distributed in all types of environments. Their use has proved to be an effective method for controlling zoonotic bacteria, since they have unique advantages compared to the antimicrobials (Atterbury, 2007). The advantages of phage-therapy include specificity, and bacteriophages may be strain-specific or species-specific. This characteristic is of great importance because it avoids the imbalance of the intestinal microbiota, contrary to that frequently caused by broad-spectrum antimicrobials (Atterbury, 2007; Kutter & Sulakvelidze, 2005). Also, the bacteriophages replicate while the bacterium is viable, i.e. when it is eliminated, the phages are naturally self-limiting (Atterbury, 2007). Bacteriophages are not toxic to animals or humans, as they only attack bacteria. On the other hand they have the capacity to increase their initial concentration, so that on infecting bacteria they multiply within them until they are eliminated (Kutter & Sulakvelidze, 2005; Summers, 2001); the advantage obtained from the aforementioned process is reduction of the initial doses necessary for eliminating the bacterial contaminations.

In this connection, various compositions have been reported that comprise specific phages or combinations of phages that are used for controlling bacteria, especially *Salmonella*. One of the cases reported corresponds to patent WO2013024304, which discloses the use of bacteriophages for lysis of the bacterium *Salmonella*. That document discloses compositions that comprise bacteriophages selected from ΦSH17, ΦSH18, ΦSH19 or a variant of one of these bacteriophages, wherein the variant retains the phenotypic characteristics of the parent bacteriophage. Moreover, patents US20090297561, WO2005024005, U.S. Pat. No. 8,293,515, U520080118468, U520130336932, U.S. Pat. Nos. 8,685,696, 8,597,928 and WO2013014273 describe various types of bacteriophages that have specific activity against *Salmonella* and that are used, moreover, for preparing compositions useful for control, and treatment of infection in animals or humans as well as in the colonization of processed and unprocessed food products by *Salmonella*, or colonization of equipment involved in the processing of said food products.

Moreover, patent RU2232808 teaches a biological preparation for treating and preventing *salmonellosis* in farm animals and poultry, wherein said biopreparations contain various strains of bacteriophages, which are used in an effective amount.

In this class of ideas, patent WO2013169102 relates to a bacteriophage, a polypeptide and a corresponding polynucleotide, a nucleic acid molecule and/or vector and/or cell that comprises said polynucleotide, a composition that comprises said bacteriophage, polypeptide, polynucleotide, construct, vector and/or cell, for the prevention, treatment or diagnosis of contamination with *Salmonella*.

Finally, there are also documents such as patent US20140220659, which discloses a method for preparing a strain of bacteriophages specific to a selected bacterial strain, strains of bacteriophages obtained in this way and the use of bacteriophages for preparing a preparation for the prevention and treatment of infections of farm animals, especially poultry, with strains of pathogenic bacteria that are sensitive to these bacteriophages. Moreover, this document provides technology for production of an antimicrobial preparation suitable for use as a feed additive for poultry and pigs, which at the same time is specific to the pathogenic strains of *Salmonella* that cause the occurrence of *salmonellosis*, especially in human beings.

BRIEF DESCRIPTION OF THE INVENTION

The main aim of the present invention is to provide a new cocktail of bacteriophages with bactericidal activity against serovars of *Salmonella enteritidis, Salmonella typhimurium* and *Salmonella paratyphi* B. The cocktail contains bacteriophages resistant to chlorine and stable at ambient conditions and at 4° C. Therefore the new cocktail may be used prophylactically for preventing colonization of the strains of *Salmonella* in farm animals, poultry and eggs.

An additional aim of the invention is to block the cycle of colonization of pathogenic bacteria in farm animals and poultry by reducing and/or eliminating the transmission of bacterial pathogens during the life cycle of farm animals and birds.

Another aim of the invention is to reduce, eliminate or prevent the colonization of eggs by bacterial pathogens such as *Salmonella enteritidis* and *Salmonella typhimurium* and *Salmonella paratyphi* B.

An additional aim of the invention is to minimize or eliminate the strains of *Salmonella enteritidis, Salmonella typhimurium* and *Salmonella paratyphi* B that colonize farm animals, eggs and poultry, by the application of the new cocktail of bacteriophages in the environment of the farm animals, hens, eggs and poultry.

An additional aim of the invention is to prevent and eliminate the strains of *Salmonella enteritidis, Salmonella typhimurium* and *Salmonella paratyphi* B that contaminate plant, equipment and machinery involved in the production process of animals for human consumption, such as chicken and eggs, by using the new cocktail of phages as disinfectant in work areas of farms, on surfaces in abattoirs and in processed foods.

It is an aim of the invention to provide alternatives for improving the health of farm animals and for reducing, eliminating or preventing the mortality thereof.

The present invention provides a collection of bacteriophages that can make up a cocktail of various bacteriophages against *Salmonella enteritidis, Salmonella typhimurium* and *Salmonella paratyphi* B.

To achieve these aims, the present invention is directed at the presentation and/or application of a new cocktail of bacteriophages during the production of poultry and/or eggs for reducing, eliminating or preventing the colonization of bacterial pathogens such as *Salmonella enteritidis, Salmonella typhimurium* and *Salmonella paratyphi* B. The term "production" as applied to poultry includes, but is not limited to reproduction, rearing, storage, processing and handling of poultry and all the associated functions. The term "production" as applied to eggs includes, but is not limited to incubation, storage and processing of eggs for consumption and all the associated functions. The term "poultry" includes, but is not limited to fattening chicken, hens and breeding hens. Bacterial colonization refers to the initial exposure of a pathogen and the initial growth and expansion of the population of the microorganism or microorganisms. After colonization, infection occurs, and the bacterial population alters the homeostasis of the host and produces adverse symptoms.

In view of the foregoing, the subject matter for protection corresponds to a new cocktail of phages that comprises bacteriophages of the order Caudovirales, that have lytic activity against various strains of *Salmonella enteritidis, Salmonella typhimurium* and *Salmonella* paratyphi B. Said cocktail may be used for industrial application, and is administered by means of liquid media such as sprays, buffers or water, and solids such as powder or pellets. Said cocktail comprises phages from a collection of phages characterized and selected for their efficacy and their absence of virulence or toxicity genes.

DETAILED DESCRIPTION OF THE INVENTION

Figure 1:
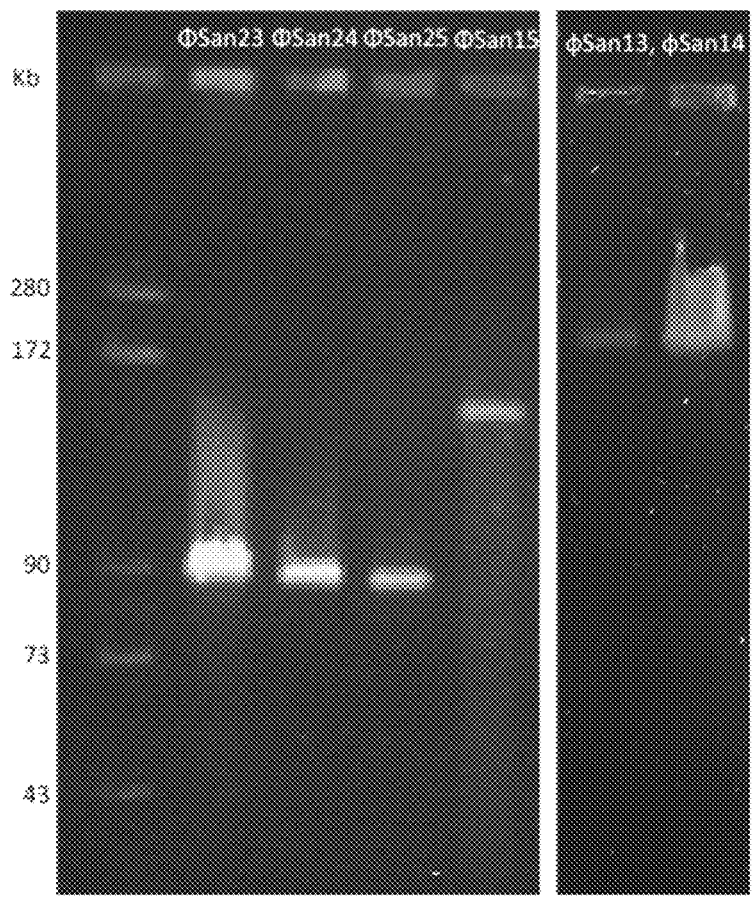
FIG. 1. PFGE of the 6 phages of the invention, φSan13 (SEQ ID NO: 1), φpSan14 (SEQ ID NO: 2), φpSan15 (SEQ ID NO: 3), φpSan23 (SEQ ID NOs: 4 AND 5), φpSan24 (SEQ ID NO: 6) and φpSan25 (SEQ ID NO: 7).

The present invention relates to a new cocktail of bacteriophages with specific lytic activity against *Salmonella enteritidis, Salmonella typhimurium* and *Salmonella paratyphi* B., for reducing, eliminating and/or preventing them in farm animals, poultry and eggs.

The new cocktail is made up of bacteriophages selected from a collection of phages, all belonging to the order Caudovirales.

The present invention discloses compositions of bacteriophages that comprise excipients and 6 phages, designated hereinafter as φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

In addition, the genomes are free from toxicity and virulence genes, which makes them ideal for industrial application as they are safe for animals that consume them and for humans who consume the poultry products.

Tests in vivo demonstrated the harmlessness of the cocktail of phages in farm birds. There were no differences in mortality relative to the control group without phages and there were no sick birds on being exposed to the phages. The safety and harmlessness of the phages of the present invention were thus confirmed.

On the other hand, the cocktail of phages makes it possible to counteract bacterial resistance, in contrast to antibiotics and disinfectants. Based on the foregoing, the phages that make up the cocktail may be replaced with any of the phages in the collection when this is necessary to minimize the risk of development of resistance.

It remains stable at 4° C. for two years and at ambient temperature of 20° C. for 1 month. Stability at pH 7.0 is maintained for one year.

The phages are stable in the chlorinated water that the farm animals drink (chlorine concentration 0.000975%) and they remain viable for 24 h.

The efficiency in vitro of the cocktail of bacteriophages decreases the bacterial population of *Salmonella* between 3.33 and 4.62 log 10 CFU/ml during 10 hours of exposure to the cocktail.

Testing in vivo in poultry showed that administration of the cocktail of phages of the invention increased the weight of the birds by 70 grams relative to the control. Average weight of the control at the end of the production cycle: 2.252±125 g and average weight of the treatment with phages at the end of the production cycle: 2.322±121 g.

Moreover, tests in vivo in poultry showed a difference in the conversion and/or feed efficiency of the birds, with the birds exposed to the phages having a better efficiency than the birds of the control without phages.

A result additional to the tests in vivo was the observation of greater uniformity in the weight of the birds that were administered the cocktail of phages of this invention, than the birds of the control without phages.

The excipients that accompany the cocktail of phages in the composition are selected from a solvent or a buffer. For example, it is a solution consisting of 5.8 g NaCl, 5 ml of 2% gelatin, 50 ml 1M Tris-HCl, pH 7.5, 1.2 g $MgSO_4$ $7H_2O$ (Kutter & Sulakvelidze, 2005).

The size of the genomes of the phages usually varies between 30 and 180 kb. The new cocktail or composition of bacteriophages comprises the phages: φSan13 (SEQ ID NO: 1) with a genome size of 170 kb, φSan14 (SEQ ID NO: 2) with a genome size of 170 kb, φSan15 (SEQ ID NO: 3) with a genome size of 159.3 kb, φSan25 (SEQ ID NO: 7) with a genome size of 86.7 kb, φSan23 (SEQ ID Nos: 4 and 5) with a genome size of 90 kb and φSan24 (SEQ ID NO: 6) with a genome size of 90 kb, and an additional component, such as an excipient that is selected from a solvent or a buffer.

It may be administered by means of liquid media such as sprays, buffers, or water, and solid media such as powder or pellets to be administered in the feed.

One embodiment of the invention is the use of the composition of bacteriophages φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7) for the control of *Salmonella enteritidis, Salmonella typhimurium* and *Salmonella paratyphi* B, on surfaces, plant, equipment and machinery that are present in farms for animals, especially poultry farms.

Another embodiment of the invention is the use of the composition of bacteriophages φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7) for the control and/or elimination of *Salmonella enteritidis, Salmonella typhimurium* and *Salmonella* paratyphi B, in farm animals, poultry, eggs and processed foods and the packaging thereof.

In another embodiment of the invention, the composition of bacteriophages φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), or φSan25 (SEQ ID NO: 7) for the prevention of *Salmonella enteritidis, Salmonella typhimurium* and *Salmonella paratyphi* B, is used in farm animals, poultry, eggs and processed foods and the packaging thereof.

One embodiment of the invention also comprises a composition of bacteriophages φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7) in a dose of $10^7$-$10^9$ PFU/mL.

Moreover, another embodiment of the invention corresponds to a liquid or solid feed supplement that comprises a composition of bacteriophages that comprises between one and six bacteriophages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

Moreover, another embodiment of the invention corresponds to a disinfectant that comprises a composition of bacteriophages that comprises between one and six bacteriophages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

In a preferred embodiment of the invention, the composition of bacteriophages for the prevention, elimination and/or reduction of infections and contaminations caused by *Salmonella enteritidis, Salmonella typhimurium* and *Salmonella paratyphi* B is characterized in that it comprises at least one of the six lytic phages against *Salmonella*, φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), or φSan25 (SEQ ID NO: 7); or between 1 and 6 phages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

In another embodiment of the invention, the cocktail of bacteriophages for the prevention, elimination and/or reduction of infections and contaminations caused by *Salmonella enteritidis, Salmonella typhimurium* and *Salmonella paratyphi* B is characterized in that it comprises at least 2 of the 6 lytic phages against *Salmonella*, φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), or φSan25 (SEQ ID NO: 7); or between 2 and 6 phages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

In a different embodiment of the invention, the composition of bacteriophages for the prevention, elimination and/or reduction of infections and contaminations caused by *Salmonella enteritidis, Salmonella typhimurium* and *Salmonella paratyphi* B is characterized in that it comprises at least 3 of the 6 lytic phages against *Salmonella*, φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), or φSan25 (SEQ ID NO: 7); or between 3 and 6 phages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

In a different embodiment of the invention, the composition of bacteriophages for the prevention, elimination and/or reduction of infections and contaminations caused by *Salmonella enteritidis, Salmonella typhimurium* and *Salmonella paratyphi* B is characterized in that it comprises at least 4 of the 6 lytic phages against *Salmonella*, φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), or φSan25 (SEQ ID NO: 7); or between 4 and 6 phages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

Finally, in another preferred embodiment of the invention, the cocktail of bacteriophages for the prevention, elimination and/or reduction of infections and contaminations caused by *Salmonella enteritidis, Salmonella typhimurium* and *Salmonella paratyphi* B is characterized in that it comprises the 6 lytic phages against *Salmonella*, φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), or φSan25 (SEQ ID NO: 7).

Similarly, the present composition of bacteriophages for the prevention, elimination and/or reduction of infections and contaminations may also comprise additional phages selected from the order Caudovirales that have lytic activity against various strains of *Salmonella enteritidis, Salmonella typhimurium* and *Salmonella* paratyphi B.

In one embodiment of the invention, the composition of phages comprises only phages selected from the set φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7).

Additionally, in another embodiment of the invention, said composition is characterized in that each of the phages is in an equal proportion.

Moreover, in another embodiment of the invention, the composition is characterized in that each of the phages is in a different proportion.

Thus, Table 1, presented below, contains the particular characteristics of each of the phages of interest, which allow specific differentiation thereof with respect to all the various types of phages that may occur.

TABLE 1

Characteristics of the bacteriophages against *S. enteritidis, S. typhimurium* and *S. paratyphi* B

| Associated sequence | Name of phage | Genome size (kb) | *Index of infection (0-1) | **Index of efficiency of plating (EOP) (0-1) | Virulence or toxicity genes (yes/no) | Infecting strains of *Salmonella* |
|---|---|---|---|---|---|---|
| SEQ ID Nos: 4 and 5 | φSan23 | 90 | 0.72 (13/18) | 0.92 (12/13) | NO | *S. enteritidis* and *S. typhimurium* |
| SEQ ID NO: 6 | φSan24 | 90 | 0.66 (12/18) | 0.67 (8/12) | NO | *S. enteritidis* and *S. typhimurium* |
| SEQ ID NO: 7 | φSan25 | 86.7 | 0.66 (12/18) | 0.58 (7/12) | NO | *S. enteritidis* and *S. typhimurium* |

TABLE 1-continued

Characteristics of the bacteriophages against *S. enteritidis, S. typhimurium* and *S. paratyphi* B

| Associated sequence | Name of phage | Genome size (kb) | *Index of infection (0-1) | **Index of efficiency of plating (EOP) (0-1) | Virulence or toxicity genes (yes/no) | Infecting strains of *Salmonella* |
|---|---|---|---|---|---|---|
| SEQ ID NO: 3 | φSan15 | 159.3 | 0.78 (14/18) | 0.57 (8/14) | NO | *S. enteritidis* and *S. typhimurium* |
| SEQ ID NO: 1 | φSan13 | 170 | 1 (5/5) | 1 (5/5) | NO | *S. enteritidis, S. typhimurium* and *S. paratyphi* B |
| SEQ ID NO: 2 | φSan14 | 170 | 0.8 (4/5) | 1 (4/4) | NO | *S. enteritidis, S. typhimurium* and *S. paratyphi* B |

*Index of infection: is calculated by dividing the number of strains of *Salmonella* that the phage infects, over the total number of strains evaluated.
**Index of the efficiency of plating (EOP): is calculated by dividing the number of strains of *Salmonella* that the phage infects with EOP ≥ 1, over the number of strains evaluated that the phage infects, without taking the EOP into account. Efficiency of plating (EOP): is the ratio of the titer of the phage in the strain evaluated and the titer of the phage in the original strain isolated.

EXAMPLES

Example 1: Characterization by Genome Size

The size of the genome of the phages is determined by pulsed-field gel electrophoresis (PFGE), based on the protocol of Evergreen Phage Lab (Olympia, Wash.) from 2009. The phages were taken at a concentration of $10^9$ pfu/ml. Then agarose plugs were prepared, which contained 400 µl of the suspension of the phage and 400 µl of agarose at 1% (w/v) (Ultra Pure DNA Grade Agarose: BioRad #162-0137) in 0.5% of TBE buffer. After lysis with proteinase K (Promega), at a final concentration of 0.1 mg/ml, washings with lysis buffer were carried out. The PFGE run conditions were as follows: 6 volts, 15 h, 2 s initial switch time and 10 s final switch time. The gel was stained with gelRed (Biotium) 3× and was visualized in the GelDoc System (Bio-Rad).

According to PFGE of the 6 phages of the invention, φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 5) and φSan25 (SEQ ID NO: 7), the genome size was 170; 170; 159.3; 90; 90 and 86.7 kb, respectively (FIG. 1).

Example 2. Transmission Electron Microscopy

The pure phages at a concentration of $10^{10}$-$10^{11}$ pfu/ml were placed on a grid covered with carbon of electrons and negative staining was performed with 1% of phosphotungstic acid. After drying, the preparations were examined with the transmission electron microscope (TEM). The morphology of the phages and their dimensions were recorded.

Figure 2:
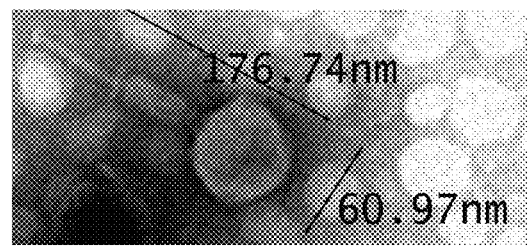
FIG. 2. Transmission electron microscopy of a phage

The phages φSan15 (SEQ ID NO: 3), φSan23 (SEQ ID NOs: 4 and 5), φSan24 (SEQ ID NO: 6) and φSan25 (SEQ ID NO: 7), which form part of this invention, belong morphologically to the family Myoviridae of the order Caudovirales (FIG. 2). The electron micrographs show that the phages have icosahedral heads with dimensions between 50 and 70 nm, with long contractile tails, with a length between 120 and 180 nm.

Example 3. Efficiency of the Cocktail of Bacteriophages in Bacterial Reduction

A culture of *Salmonella enteritidis* (OD600=0.01) was infected with a cocktail of phages, described in this invention. A multiplicity of infection (MOI) of 0.1 was used. The culture was incubated with stirring at 37° C. for 15 h. The absorbance of the culture and the bacterial count were monitored by plating serial dilutions.

Figure 3:
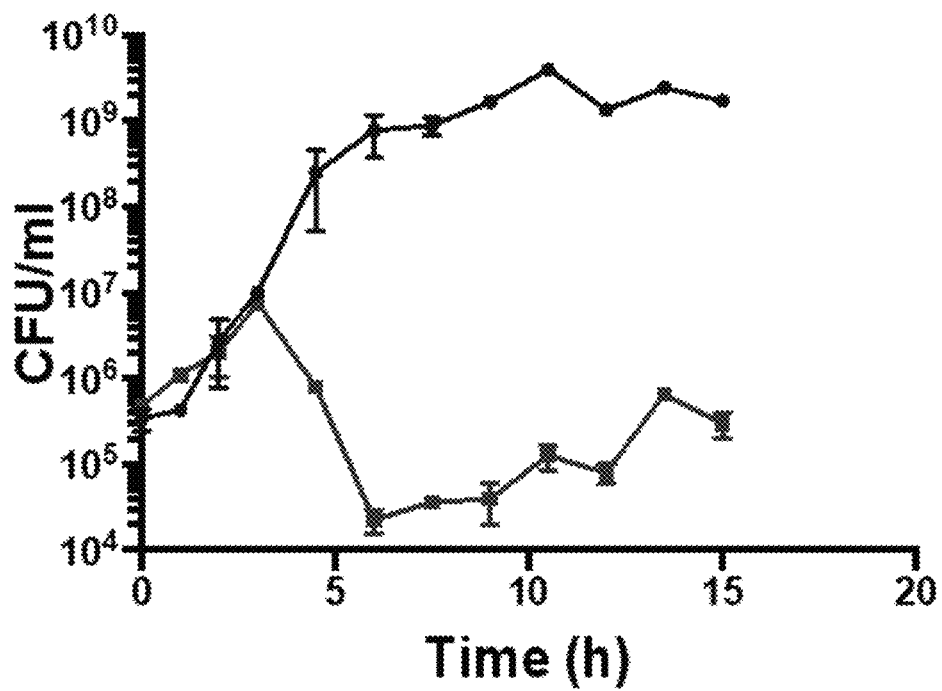
FIG. 3. Efficiency of the cocktail of bacteriophages in bacterial reduction

Reductions of *Salmonella enteritidis* of 3.12; 4.3; 3.86 and 4.29 log 10 CFU/m were obtained, among other things, after infection with the individual phages of the collection and a maximum of 4.62 log 10 CFU/ml with the cocktail of phages (FIG. 3; the culture of the bacterium without the cocktail of phages is shown in blue, and the culture of the same bacterium with the cocktail of phages is shown in red).

The combined activity of a minimum of 3 phages in the cocktail allows a greater reduction of *Salmonella* relative to the individual phages. The fact that the individual phages show lower efficiency in the elimination and/or reduction of *Salmonella* over time explains the importance of using a mixture of several phages for the composition of an efficient cocktail.

Example 4. Efficiency by Burst Size, Example of the Best Phage

Figure 4:
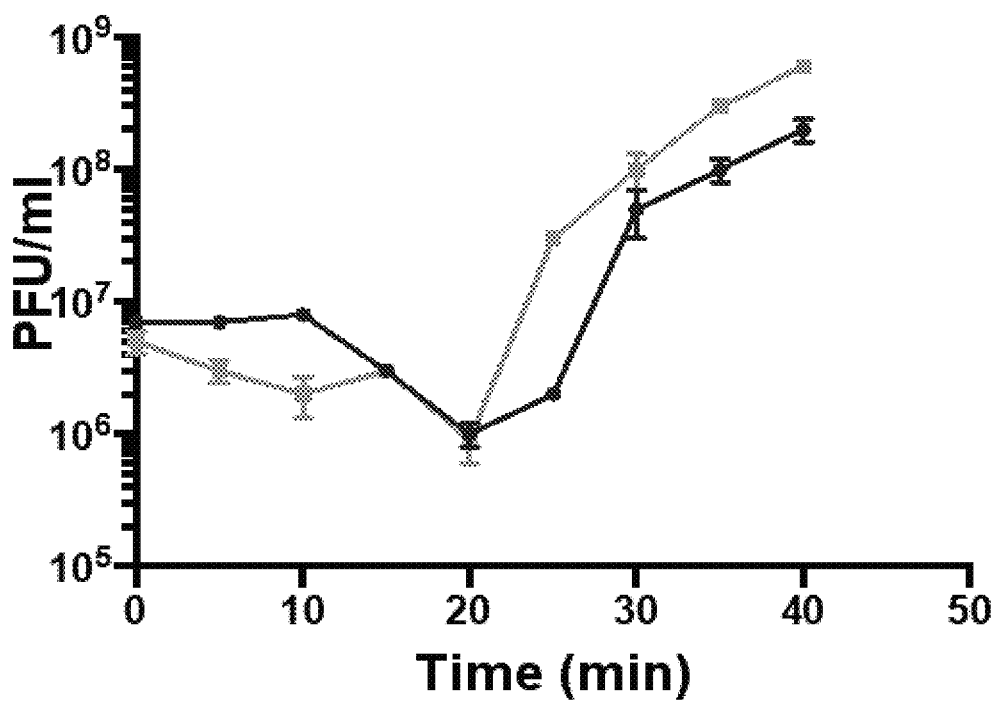
FIG. 4. Efficiency by burst size, example of the best phage

One-step curves were constructed for each of the phages φSan23 (SEQ ID NOs: 4 and 5), φSan24 (SEQ ID NO: 6), φSan25 (SEQ ID NO: 7), φSan15 (SEQ ID NO: 3), and the burst size was then calculated. The culture of *Salmonella enteritidis* s25pp (OD600=0.2) was infected with each phage, and was divided into two treatments: with and without chloroform. A multiplicity of infection (MOI) of 0.01 was used. The culture was incubated at 37° C., and samples were taken from it every 5 min for 40 min. The infected culture samples were put in chloroform and dilutions (1/10) were prepared with those without chloroform immediately in buffer SM and were plated by the double agar method. The same was done with the samples with chloroform but on the next day. Finally, a count of plaque forming units was performed (PFU/ml) and the following parameters were determined: the population growth rate of the phages (fitness), the number of progeny released (burst size), and the latent period and eclipse period arising on the unadsorbed phages and centers of infection arising from the treatment with chloroform, and on the other hand the number of unadsorbed phages arising from the treatment without chloroform (Wang et al. 2006). The burst size is an essential parameter that makes it possible to determine the level of efficiency of the phages: the higher the value, the more efficient it will be. For the phages φSan23 (SEQ ID NOs: 4 and 5), φSan24 (SEQ ID NO: 6), φSan25 (SEQ ID NO: 7), φSan15 (SEQ ID NO: 3), of the invention, they all have a high value of burst size, where in one cycle of infection of the phage, it may generate a progeny of 165 and 200 (FIG. 4); 81.6 and 120, respectively. The results show us that with these values of efficiency based on burst size, the phages of this invention are excellent candidates for the application described.

Example 5. Resistance of the Phages to Chlorine

The effect of chlorine on the infectivity of the phages of the present invention φSan23 (SEQ ID NOs: 4 and 5), φSan24 (SEQ ID NO: 6), φSan25 (SEQ ID NO: 7), φSan15 (SEQ ID NO: 3) was determined by means of two solutions of calcium hypochlorite: 1) commercial 2) directly from the pure chemical. Each of the solutions was adjusted to a final concentration of 0.000975% in sterile distilled water, which is used in the drinking troughs for poultry. The initial concentration of the commercial solution is 65%; whereas the other solution is in the pure state. Then each of the phages and the cocktail were put in each of these solutions and the viability of the phages was tested at 5 min, 15 min, 30 min, 1 hour, 2 hours and 24 hours.

The results obtained show that all the phages are infective at each of the times. The controls where only chlorinated water was sown did not show inhibition of growth of the bacterium. In Table 2, the symbol (+) represents infection of the bacterium by the phage. The results were accompanied by a description of the plaque morphology of the phage for each test performed. On reading the results, changes were observed in plaque morphology at the different times.

The results show that each of the bacteriophages is infective for up to 24 hours evaluated on 2 different samples of chlorinated water (one commercial and the other chemical). The cocktail of phages displayed constant plaque morphology over time, with clear plates, without internal growth, in contrast to the individual phages.

TABLE 2

Results of stability test in chlorine

| Phage | Time: phage in chlorinated water | | | | | |
|---|---|---|---|---|---|---|
| | 5 min | 15 min | 30 min | 1 hour | 2 hours | 24 hours |
| φSan23 (SEQ ID Nos : 4 and 5) | + | + | + | + | + | + |
| φSan24 (SEQ ID NO: 6) | + | +p | + | + | + | + |
| φSan25 (SEQ ID NO: 7) | + | + | + | + | + | + |
| φSan15 (SEQ ID NO: 3) | + | + | + | + | + | + |
| Cocktail | + | + | + | + | + | + |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10576114B2). An electronic copy of the "Sequence Listing" will also be available from the USPTO upon request and payment of the fee set forth in 37 CFR 1.19(b)(3).

The invention claimed is:

1. Composition of bacteriophages for the prevention, elimination and/or reduction of infections and contaminations caused by *Salmonella enteritidis, Salmonella typhimurium* and *Salmonella paratyphi* B, comprising phages and excipients, between 2 and 6 phages selected from the group consisting of φSan13 of SEQ ID NO: 1, φSan14 of SEQ ID NO: 2, φSan15 of SEQ ID NO: 3, φSan23 of SEQ ID NOs: 4 and 5, φSan24 of SEQ ID NO: 6, and φSan25 of SEQ ID NO: 7.

2. Composition of phages according to claim 1, wherein the composition comprises between 3 and 6 phages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

3. Composition of phages according to claim 1, wherein the composition comprises between 4 and 6 phages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

4. Composition of phages according to claim 1, wherein the composition comprises 6 phages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

5. Composition of phages according to claim 1, wherein the composition comprises additional phages belonging to the order Caudovirales.

6. Composition of phages according to claim 1, wherein the composition comprises only phages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

7. Composition of phages according to claim 1, wherein the size of the genomes of the phages varies between 30 and 180 kb.

8. Composition of phages according to claim 1, wherein each of the phages is in equal proportion.

9. Composition of phages according to claim 1, wherein each genome of the phages is free from toxicity and virulence genes.

10. Composition of phages according to claim 1, wherein the efficiency in vitro of the cocktail of bacteriophages decreases the bacterial population of *Salmonella* between 3.33 and 4.62 log 10 CFU/ml during 10 hours of exposure to the cocktail.

11. Composition of bacteriophages according to claim 1, wherein the phages that make up the composition infect a minimum of 50% of the strains evaluated with an efficiency of plating (EOP) greater than or equal to 1.

12. Composition of bacteriophages according to claim 1, wherein the excipient is selected from a solvent or a buffer.

13. Composition of bacteriophages according to claim 1, wherein the composition is administered in liquid, spray or solid form.

14. Composition of bacteriophages according to claim 1, wherein the composition comprises a composition of bacteriophages selected from the group consisting of φSan13 (SEQ ID NO: 1), φSan14 (SEQ ID NO: 2), φSan15 (SEQ ID NO: 3), φSan23 (SEQ ID NOs: 4 and 5), φSan24 (SEQ ID NO: 6), and φSan25 (SEQ ID NO: 7), in a dose of $10^7$-$10^9$ PFU/mL.

15. A method for controlling *Salmonella enteritidis, Salmonella typhimurium* and *Salmonella paratyphi* from surfaces, plant, equipment and machinery present in farms for animals comprising applying the composition of bacteriophages according to claim 1.

16. A method for controlling or eliminating *Salmonella enteritidis, Salmonella typhimurium* and *Salmonella paratyphi* B in farm animals, poultry comprising administering the composition of bacteriophages according to claim 1.

17. A method for controlling or eliminating *Salmonella enteritidis, Salmonella typhimurium* and *Salmonella paratyphi* B in eggs, processed foods and the packaging thereof comprising applying the composition of bacteriophages according to claim 1.

18. A liquid or solid feed supplement and disinfectant comprising the composition of bacteriophages according to claim 1.

19. A feed supplement that comprises a composition of bacteriophages that comprises between two and six bacteriophages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

20. A disinfectant that comprises a composition of bacteriophages that comprises between two and six bacteriophages selected from the group consisting of φSan13 (SEQ ID NO: 1), φSan14 (SEQ ID NO: 2), φSan15 (SEQ ID NO: 3), φSan23 (SEQ ID Nos: 4 and 5), φSan24 (SEQ ID NO: 6), and φSan25 (SEQ ID NO: 7).

* * * * *